United States Patent
Biedermann

(10) Patent No.: US 11,432,856 B2
(45) Date of Patent: Sep. 6, 2022

(54) BONE PLATE WITH ACCESSORY ELEMENTS ATTACHED AT BONE FASTENER HOLES

(71) Applicant: Biedermann Technologies GmbH & Co. KG, Donaueschingen (DE)

(72) Inventor: Markku Biedermann, Miami, FL (US)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 311 days.

(21) Appl. No.: 16/794,077

(22) Filed: Feb. 18, 2020

(65) Prior Publication Data

US 2020/0275957 A1     Sep. 3, 2020

Related U.S. Application Data

(60) Provisional application No. 62/812,060, filed on Feb. 28, 2019.

(51) Int. Cl.
*A61B 17/80*     (2006.01)
*A61B 17/86*     (2006.01)

(52) U.S. Cl.
CPC ...... *A61B 17/8047* (2013.01); *A61B 17/8042* (2013.01); *A61B 17/8061* (2013.01); *A61B 17/8605* (2013.01); *A61B 17/8625* (2013.01)

(58) Field of Classification Search
CPC ............ A61B 17/8047; A61B 17/8042; A61B 17/8061; A61B 17/809
See application file for complete search history.

(56) References Cited

U.S. PATENT DOCUMENTS

| 8,808,335 | B2 | 8/2014 | Biedermann |
| 9,526,544 | B1 | 12/2016 | Kumar |
| 2017/0333097 | A1 | 11/2017 | Orbay et al. |
| 2018/0092676 | A1* | 4/2018 | Ananthan .......... A61B 17/8085 |
| 2018/0161082 | A1 | 6/2018 | Biedermann |

OTHER PUBLICATIONS

European Search Report and European Search Opinion for Appl. No. 20159539.4-1132, dated Aug. 3, 2020, 12 pages.

* cited by examiner

*Primary Examiner* — Olivia C Chang
(74) *Attorney, Agent, or Firm* — Gordon & Jacobson, P.C.

(57) ABSTRACT

A bone plate assembly is provided for stabilizing a bone fracture. The bone plate assembly includes a bone plate, a first fastener, a second fastener, and an accessory element. The bone plate has a bone contacting, lower surface and an opposite upper surface, and a plurality of screw extending through the bone plate from the upper surface to the lower surface. At least one of the screw holes, a first fastener extends through the bone plate and into an underlying bone or bone fragment. Further, at the same screw hole, a second fastener is received to couple the accessory element to the upper surface of the bone plate to stabilize the accessory element on the bone plate. In at least an embodiment, the accessory element extending over a perimeter of the bone plate and into contact with the bone.

15 Claims, 10 Drawing Sheets

BONE PLATE WITH ACCESSORY ELEMENTS ATTACHED AT BONE FASTENER HOLES

CROSS-REFERENCE TO RELATED APPLICATION

This application claims benefit of U.S. Provisional Application 62/812,060, filed Feb. 28, 2019, which is hereby incorporated by reference herein in its entirety.

BACKGROUND OF THE INVENTION

1. Field of the Invention

The present invention relates to surgical devices and systems to aid in healing a fractured bone. More particularly, this invention relates to a bone plate and fasteners for securing the bone plate to a bone. In addition, this invention relates to supplemental extension members that are secured to the bone plate to aid in healing the bone.

2. State of the Art

Bone fractures are often treated with bone plates that stabilize and support the components of a fractured bone in a reduced position during healing. Numerous plates are known for this purpose. Moreover, plates are specifically adapted in size and configuration for the bone to be treated. By way of example, fractures at the distal radius bone are treated with plates designed to accommodate the anatomical contours of the bone so that the plate sits close to the bone and does not cause undue irritation to overlying soft tissue.

One such plate is described in co-owned U.S. Pat. No. 8,808,335, which describes a bone plate with polyaxial bone fasteners. The fasteners have a threaded shank and a spherical head with an upper driver slot. The bone plate is contoured to seat close to the bone. The bone plate has fastener holes defined by at least a lower portion in which the spherical head of a fastener can rotate, and an upper portion with a thread. The polyaxial fasteners can be inserted at any angle within a range of angles, e.g., ±35° relative to an axial center of the fastener hole; i.e., through a motion cone greater than 60°. The angle of insertion can be identified by the surgeon at the time of implantation so that bone fragments of the particular fracture are optimally engaged and supported. After a fastener is inserted, a locking element is provided and threadedly inserted into the threaded upper portion of the fastener hole and engaged against the fastener head. The locking element prevents backout of the bone fastener from the fastener hole. In addition, the locking element provides sufficient contact against the spherical head of a fastener to lock the fastener in its angular position relative to the bone plate.

Even with such improved plate designs, it may be determined that additional support of the bone is required after implantation of the plate with the bone fastener.

SUMMARY OF THE INVENTION

A bone plate assembly is provided for stabilizing a bone fracture. The bone plate assembly includes a bone plate, a first fastener, a second fastener, and an accessory element. The bone plate has a bone contacting lower surface and an opposite upper surface, and a plurality of screw holes extending through the bone plate from the upper surface to the lower surface. At at least one of the screw holes, a first fastener extends through the bone plate and into an underlying bone or bone fragment. Further, at the same screw hole, a second fastener is received to couple the accessory element to the upper surface of the bone plate to stabilize the accessory element on the bone plate. In at least an embodiment, the accessory element extends over a perimeter of the bone plate and potentially into contact with the bone.

In an embodiment, a bone plate assembly includes a bone plate, a bone fastener, a locking element, an accessory element, and a retainer. The bone plate has a screw hole having a lower portion and an upper portion. The bone fastener has a head and a shaft. The head of the fastener is supported in the lower portion of the screw hole. The locking element includes an outer portion that is rotationally engaged and secured in the upper portion of the screw hole to lock the axial position of the bone fastener relative to the plate, and an axial threaded bore. The accessory element includes an opening that is positioned over the threaded bore of the locking element. The retainer includes a threaded axial portion and a cover portion. The axial portion is positioned through the opening in the accessory element, threaded into threaded bore of the locking element, and tightened such that a portion of the accessory is held in compression between the locking element and the cover portion to fix the accessory element relative to the plate.

In another assembly, an alternative locking element is provided that eliminates the requirement for a retainer. The bone plate assembly includes a bone plate, a bone fastener, a modified locking element, and an accessory element. The bone plate has a screw hole having a lower portion and an upper portion. The bone fastener has a head and a shaft. The head of the fastener is supported in the lower portion of the screw hole. The accessory element includes an opening that is sized to permit access to the screw hole. The modified locking element includes an outer portion that passes through the opening in the accessory element and is rotationally engaged and secured in the upper portion of the screw hole. The modified locking element both locks the position of the bone fastener relative to the plate, and locks the accessory element in compression between a portion of the modified locking element and the bone plate.

In embodiments, the bone fastener is a polyaxial fastener having a head with a spherical outer surface portion. The bone fastener can be passed through the screw hole within a range of angles. The locking element operates to fix the angular position, as well as axial position, of the bone fastener relative to the plate.

In embodiments, the accessory element is a bone hook, a suture anchor, and/or a plate extender. In other embodiments, the system includes combinations of two or more accessory elements. In embodiments, the system includes two or more of like type accessory elements. In embodiments, the system includes two or more different accessory elements.

The bone plate system allows implantation of the bone plate onto a fractured bone. Then, because the accessory element can be applied to the top surface of the bone plate after the bone fasteners have already been coupled to the bone plate, the surgeon can determine after initial implantation of the bone plate whether the fracture would be further benefited by implantation of one or more accessory elements. If so, no specialized or modified plate is required. Rather, all that is required is use of a specially adapted locking element and retainer element that together permit attachment of the accessory element to the plate.

DETAILED DESCRIPTION OF EMBODIMENTS

Figure 1:
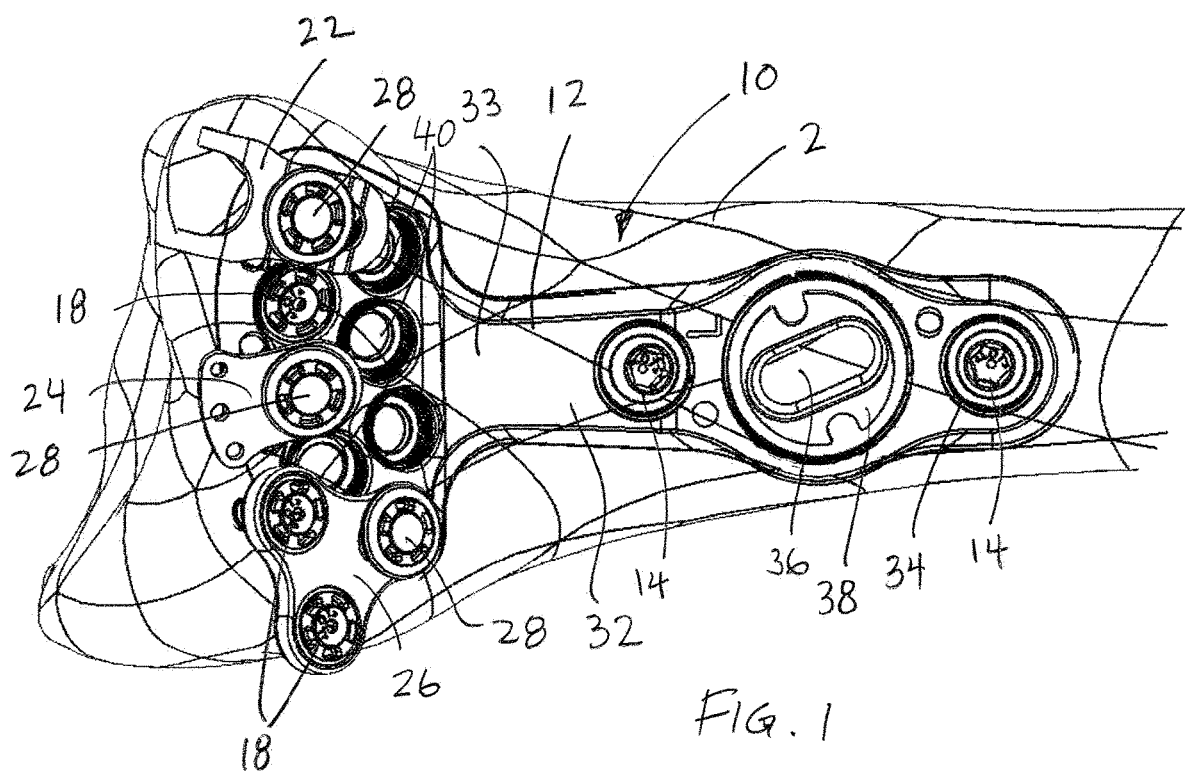
FIG. 1 shows a top view of a bone plate assembly on a distal radius bone according to an embodiment of the system.
Figure 2:
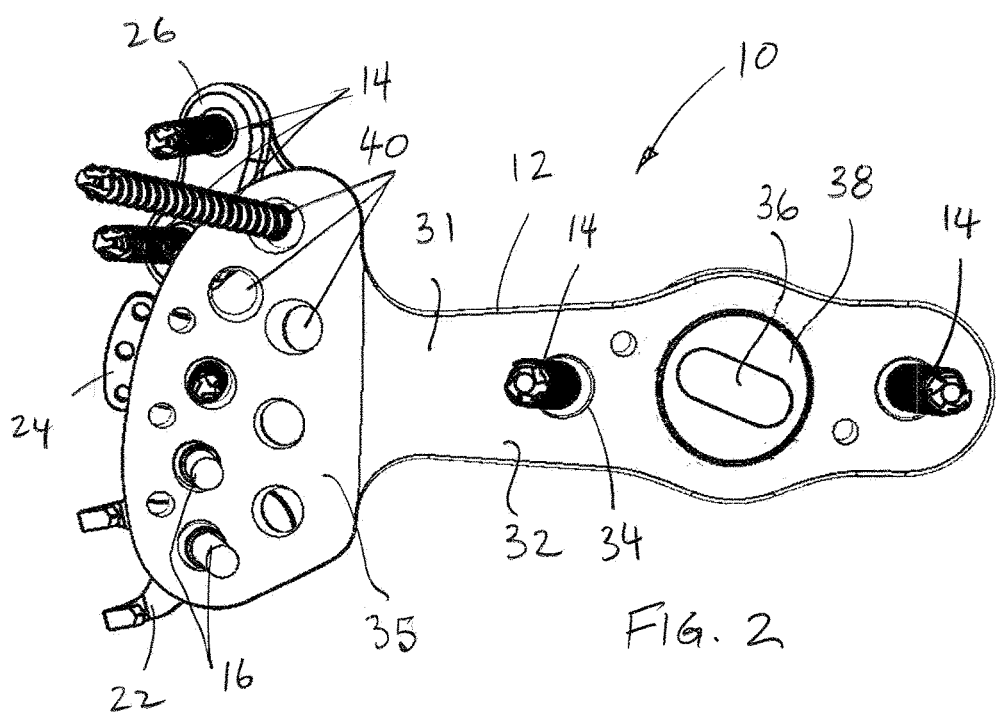
FIG. 2 shows a bottom view of the bone plate assembly of FIG. 1.

Turning now to FIGS. 1 and 2, an exemplar bone plate assembly 10 is shown according the system. The assembly 10 includes a bone plate 12, bone fasteners 14, 16, locking elements 18, 20 (see FIGS. 9-12) for retaining at least a plurality of the bone fasteners 14, 16 in a set angular orientation and axial position with respect to the bone plate 12, accessory elements 22, 24, 26 for supplemental attachment to the plate, and retainer elements 28 coupled axially relative to a locking element 20 which secures the accessory element relative to the bone plate. In FIG. 1 several accessory elements are shown; i.e., a bone hook 22, a suture anchor 24, and a plate extender 26, each of which will be described in detail below. However, such exemplar accessory elements are not intended to be limiting to the possible accessory elements that may be coupled to the plate in accord with the systems and assemblies described herein.

In the exemplar embodiment shown, bone plate 12 is a distal radius plate sized and configured for placement at the metaphysis of a distal radius bone 2. The plate has a lower bone contacting surface 31 and an opposite upper surface 33. The plate 12 has a shaft portion 32 and a head portion 35 oriented substantially traverse to the shaft portion. The shaft portion 32 has a plurality of circular first holes 34, and preferably a re-orientatable second hole 36 described in detail in co-owned US Pub. No. 2018/0161082, which is hereby incorporated by reference herein in its entirety. Briefly, the re-orientatable second hole 36 is defined within a rotatable member 38 positioned within an opening in the shaft 32. The second hole 36 is displaced on the shaft portion 32 as the rotatable member 38 is reoriented to support a head of a bone fastener 14 at various locations. The reorientable second hole 36 may be round or elongate. Other screw hole configurations can also be provided to the shaft. The head portion 35 of the plate 12 includes a plurality of third holes 40, the structure of which is described hereinafter.

Figure 3:
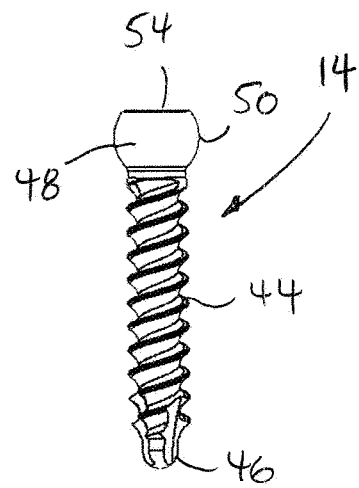
FIG. 3 is a side elevation view of a bone screw of the bone plate assembly.
Figure 4:
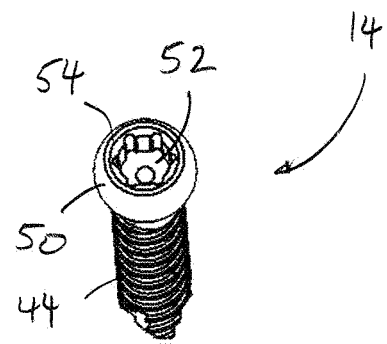
FIG. 4 is a top perspective view of the bone screw of FIG. 3.
Figure 5:
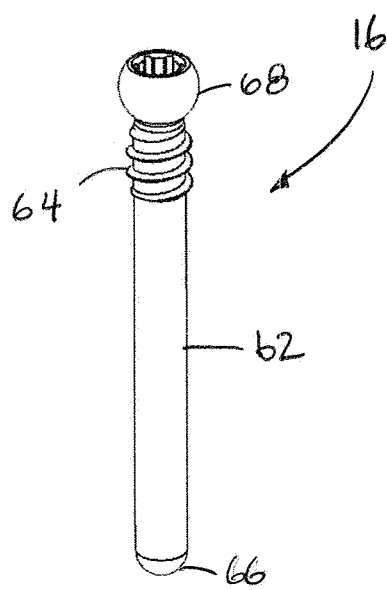
FIG. 5 is a side elevation view of a bone peg of the bone plate assembly.
Figure 6:
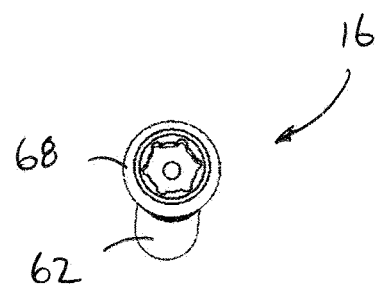
FIG. 6 is a top perspective view of the bone screw of FIG. 5.

The system 10 includes a plurality of bone anchors in the form of bone screws 14, 16 which can be inserted into the first holes 34, second holes 36, and/or the third holes 40 (FIGS. 3 and 4). The bone screw 14 has a threaded shank 44 with a self-tapping tip 46 and a head 48. The head 48 has a spherical exterior surface portion 50 and a recess 52 at its free end 54 opposite to the tip 56 for engagement with a screw driver. The system may also or alternatively include bone anchors in the form of pegs or pins 60 which can also be inserted into first holes 34, second holes 36, and/or third holes 40 (FIGS. 5 and 6). The pins 60 have a shank 62 with proximal threads 64, a blunt tip 66, and a head 68. The head 68 is substantially the same configuration as head 48. Other longitudinal bone anchors with or without any threads along the shaft can also be used.

Figure 7:
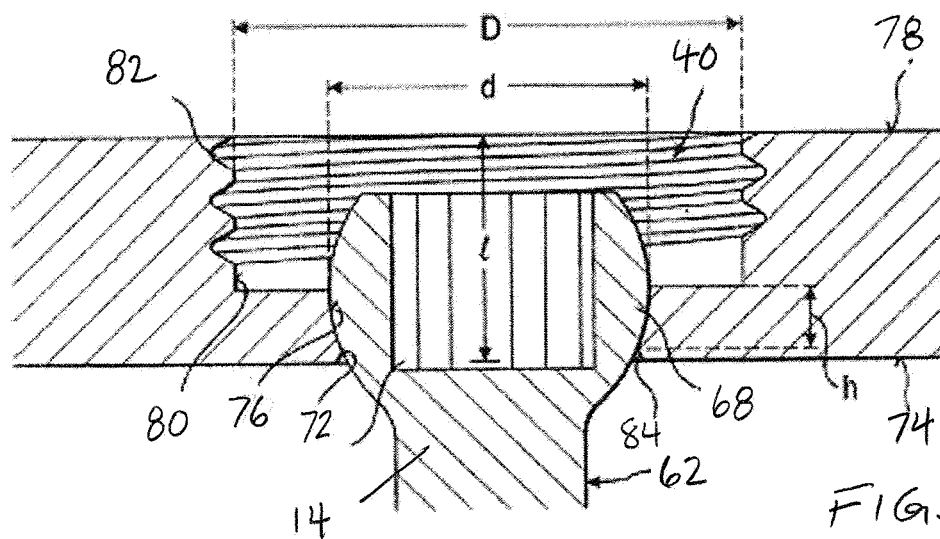
FIG. 7 is a schematic cross-section view of a bone screw hole and bone screw as provided in the head of the bone plate of the bone plate assembly.
Figure 8:
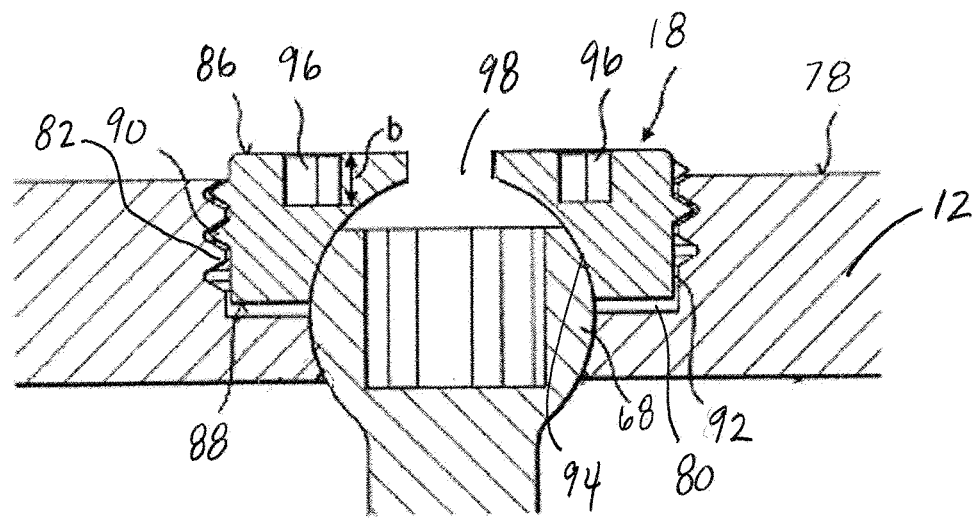
FIG. 8 is a schematic cross-section view of a bone screw hole, bone screw and locking element as provided in the head of the bone plate of the bone plate assembly.

The structure of the first holes 34 and second holes 36 is adapted to support the heads of the bone screws. Any suitable structure can be used, particularly including the structure described below with respect to the third holes 40. Turning now to FIGS. 7 and 8, the third holes 40 comprise an opening 72 at the bottom side 74 of the inner diameter, which is larger than the outer diameter of the shank 62 of the bone screw 16 so that the shank can pass therethrough. The diameter is, however, smaller than the largest outer diameter d of the head 68 so that the head cannot pass therethrough. Adjacent the opening 72 a hollow seat portion 76 is provided which forms a socket for a pivoting movement of the head 68. This allows insertion of the bone screw at any desired angle with a permitted range of angles. In the embodiment shown, the seat portion 76 is spherically-shaped with a radius that matches the radius of the spherically-shaped portion of the head 68. When the head rests in the seat portion, a part of the spherical section of the head projects out of the bottom side 74. The height h of the seat portion 76 is smaller than the radius of the head 68 and preferably smaller than half of, more preferably smaller than or equal to a quarter of the radius of the head 68. Between the seat portion 76 and the top side 78, a cylindrical bore 80 is provided with a threaded portion 82. In one exemplary aspect of the invention, this internal threaded portion 82 has a full thread, reaching to the top of the cylindrical bore 80. The inner diameter of the bore 80 is larger than the inner diameter of the seat portion 76 and larger than the outer diameter of the spherical portion of the head 68. In other words, the inner diameter D of the bore 80 is larger than the outer diameter d of the head 68. By means of this, access to the head 68 with a screw driver is possible even at large pivot angles. For example, the inner diameter D of the bore 80 may, in one exemplary aspect of the invention, be approximately 1.2 to 1.7 times larger than the maximum outer diameter d of the head 68. The bottom opening 72 widens in a conical portion 84 towards the bottom side 74 to allow even larger pivot angles for the bone screw 14.

Figure 9:
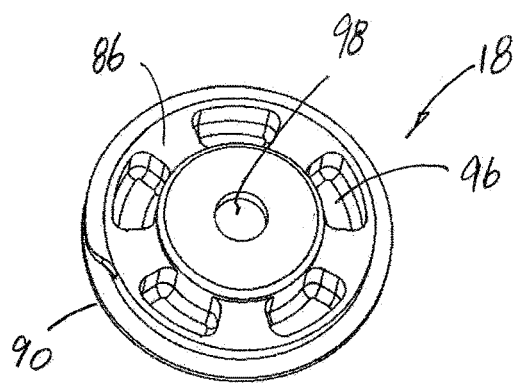
FIG. 9 is a top perspective view of a first-type locking element.
Figure 10:
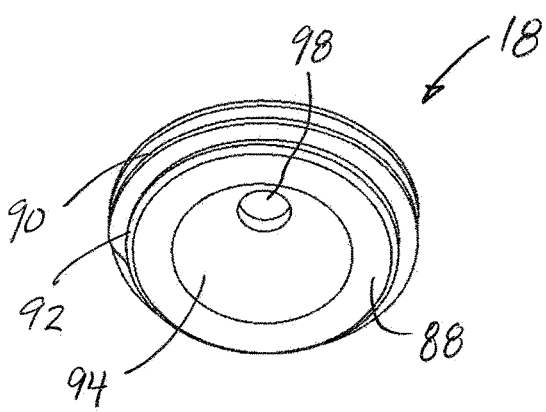
FIG. 10 is a bottom perspective view of the first-type locking element.

Turning to FIGS. 8, 9 and 10, the locking element 18 is substantially cylindrical and has a top side 86 and a bottom side 88 and a threaded exterior surface portion 90 which cooperates with the internally threaded portion 82 of the bore 80 of the screw hole in the plate 12. The height of the locking element corresponds substantially to the depth of the bore 80 so that when the locking element 18 is screwed into the bore 80 its top side 86 is substantially flush with the top side 78 of the plate member. The locking element is partially threaded. The non-threaded portion 92 is at the lower end and has an axial length which may be about equal to or smaller than that of the threaded portion 90. The locking element can also be fully threaded. On the bottom side 88 the locking element 18 comprises preferably a spherically-shaped head recess 94 which fits to the spherically-shaped portion of the head 68. The depth of the head recess 94 can be equal to or larger than the radius of the spherical portion of the head 68. By means of this, the pressure exerted by the locking element 18 onto the head 68 is smoothly distributed onto the head 68. A driver recess 96 in form of a ring-shaped arrangement of one or more slots or grooves allows a form-fit engagement of a corresponding tool is provided in the outer radial area of the top side 86 of the locking element 18. The central area of the top side is provided with an axial opening 98 or solid, i.e. is without an opening. It is possible to provide different locking elements which differ in their axial length or a different depth in the spherically-shaped head recess to achieve either full locking of the head or a frictional locking. Frictional locking allows pivoting under application of an additional force which exceeds the frictional force between head and plate member. A further different locking element may have a length or a different depth in the spherically-shaped recess which allows a free pivotal movement of the screw with the locking element only preventing pull-out of the screw.

Figure 11:
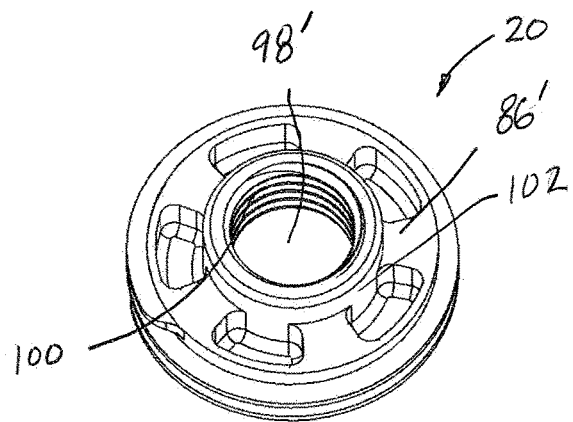
FIG. 11 is a top perspective view of a second-type locking element.
Figure 12:
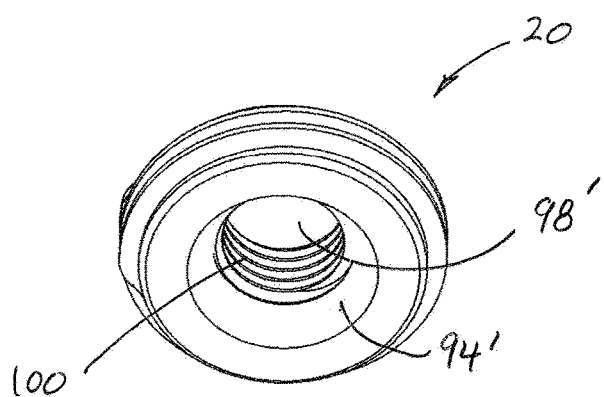
FIG. 12 is a bottom perspective view of the second-type locking element.

Turning now to FIGS. 11 and 12, a second-type of locking element 20 is shown. Second-type of locking element 20 is substantially similar to locking element 18 with the exception of the following differences. First, locking element 20 has a relatively larger axial opening 98'. Second, the axial opening 98' is provided with threads 100. Third, the axial opening 98' may extend upwards as a tubular extension 102 above the upper surface 86' of the locking element to allow mounting of one of the accessory elements 22, 24, 26 thereon (as described hereinafter) and to provide additional surface area for thread 100 formation. Fourth, because the axial opening 98' is larger than any axial opening 98 in locking element 18, the area of the head recess 94' is reduced to more peripheral regions for contact against the head 68 of the screw 16. All other features may remain the same; but are not limited to being the same.

Figure 13:
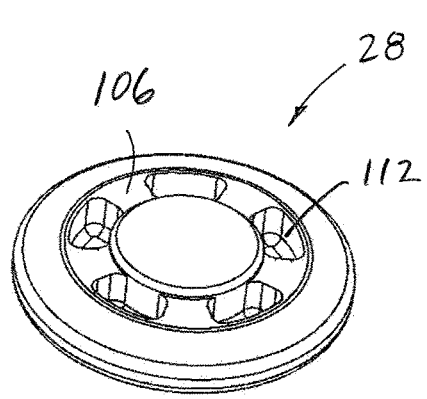
FIG. 13 is a top perspective view of a retainer element for use in association with the second-type locking element.
Figure 14:
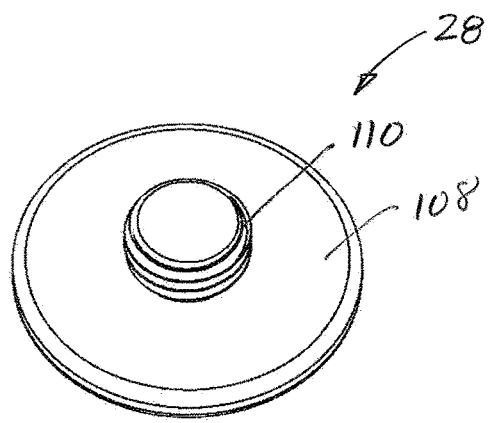
FIG. 14 is a bottom perspective view of the retainer element of FIG. 13.

Referring to FIGS. 13 and 14, the retainer element 28 for use in association with the second-type locking element 20 is shown. Retainer element 28 is substantially cylindrical and has a top side 106 and a bottom side 108. A threaded screw shaft 110 extends from bottom side 108 and is sized for threaded engagement within axial opening 98'. The bottom side 108 extending peripherally about screw shaft 110 is flat, but may be textured. A driver recess 112 in form of a ring-shaped arrangement of one or more slots or grooves is provided in the outer radial area of the top side 106 of the retainer element 28. The driver recess 112 is preferably of a same form as driver recess 96 such that a common driver tool can be used for both locking elements 18, 20 as well as the retainer element 28. The retainer element 28 is adapted to secure an accessory element 22 relative to the second-type locking element 20, as now described.

Figure 15:
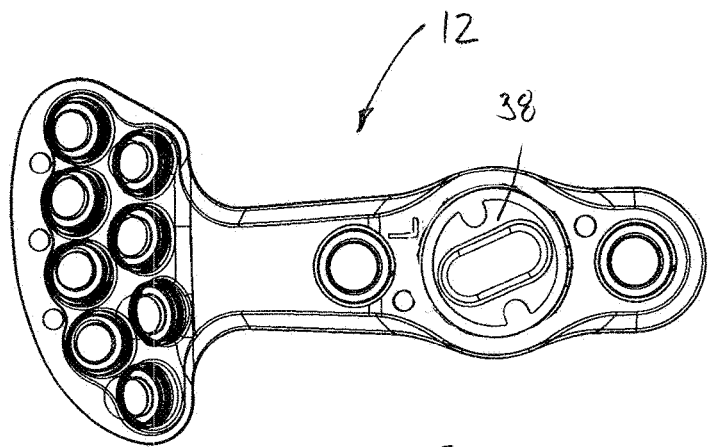
FIG. 15 is top view of a bone plate of a system.
Figure 16:
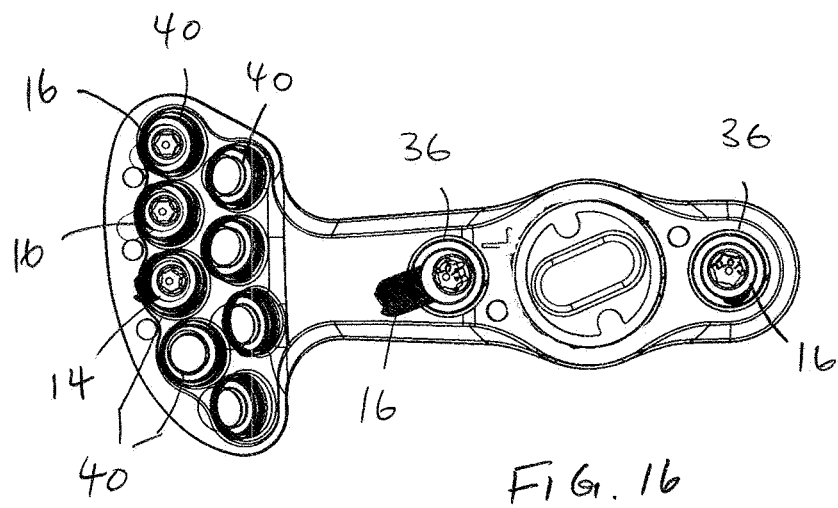
FIG. 16 is a top view of the bone plate provided with bone anchors.
Figure 17:
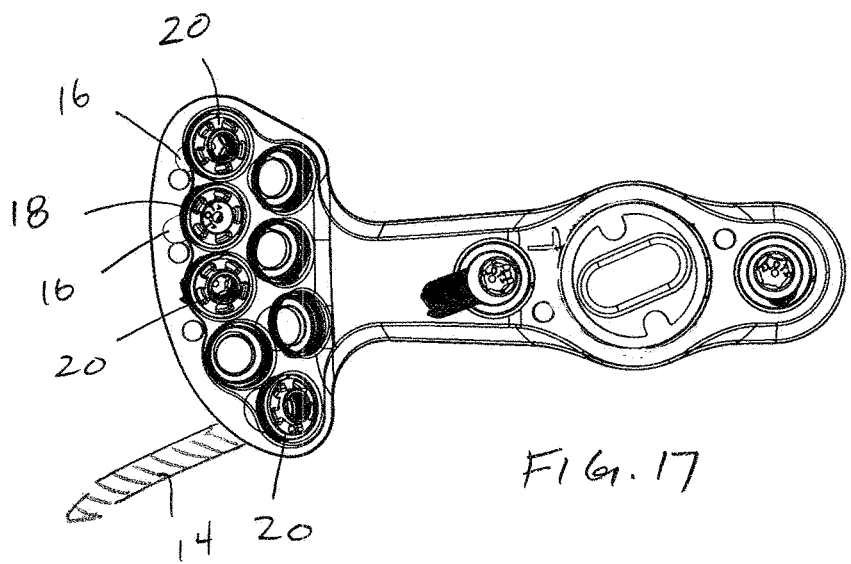
FIG. 17 is a top view of the bone plate assembled with a first-type locking element and second-type locking elements in screw holes over bone anchors.

Turning now to FIG. 15, the bone plate 12 is shown ready for use. The plate is preferably provided pre-installed with the rotatable member 38. The number of bone fasteners necessary for the stabilization of the bone or bone fragments is determined and provided. In an exemplar use, the distal radius plate is positioned on the distal radius bone (as shown in FIG. 1) and pilot holes are drilled by the surgeon through the screw holes at respective angles that are determined to position fasteners to best support and stabilize the bone fracture. Once the necessary number and types of the bone fastener are determined and pilot holes are drilled, the fasteners 14, 16 are inserted into the first holes 36, second holes 38, and third holes 40. In the provided example, shown in FIG. 16, bone screws 16 of appropriate length are inserted through several holes 36, 40 in the shaft portion 32 and head portion 35 of the plate, and one or more bone pegs 18 are inserted through other holes 40 in the head portion 35. The spherical seat 76 (FIG. 7) in the holes allows placement of the heads 48, 68 (and shafts) of the screws in the hole at the appropriate angle. After full insertion of bone fasteners, the head 48, 68 of each bone fastener abuts against the seat portion 76 of the holes 36, 40. Already in this condition, the angle between the bone fasteners 14, 16 and the plate member 12 is fixed when at least two bone fasteners are inserted. It should be noted that in some cases it is not necessary to use all the holes provided on the plate member. Holes which are not used for bone fasteners may be closed by a plug member (not shown).

After the bone fasteners are implanted, it may be determined that additional fracture stabilization or bone support is desirable. If additional support is required under unfilled screw holes of the plate, additional screws can be inserted into such screws to provide increased support. However, if additional bone support or soft tissue support is seen to be required beyond the perimeter of the plate, an accessory element can be readily attached at either or both of the filled or unfilled screw holes. This is particularly advantageous for the screw holes extending about the periphery of the plate, as such accessory elements can provide structure not provided on the standard plate but which may be useful for special situations.

For screws holes at which no accessory element is required, the connection between the bone screw and the plate can be further stabilized with the first-type locking element 18. That is, first-type locking element 18 is inserted into the threaded portion of bore of such screw holes and tightened so that it abuts against the head 68 of the bone fastener 16 to lock the fastener in the selected angular position.

For screws holes at which it is considered advantageous to have an accessory element, the connection between the bone fastener 14, 16 and the plate 12 can be further stabilized with the second-type locking element 20 such that second-type locking element is inserted into the bore of the hole and is tightened so that it locks the head 68 of the bone fastener 16 in the selected angular and axial position.

Figure 18:
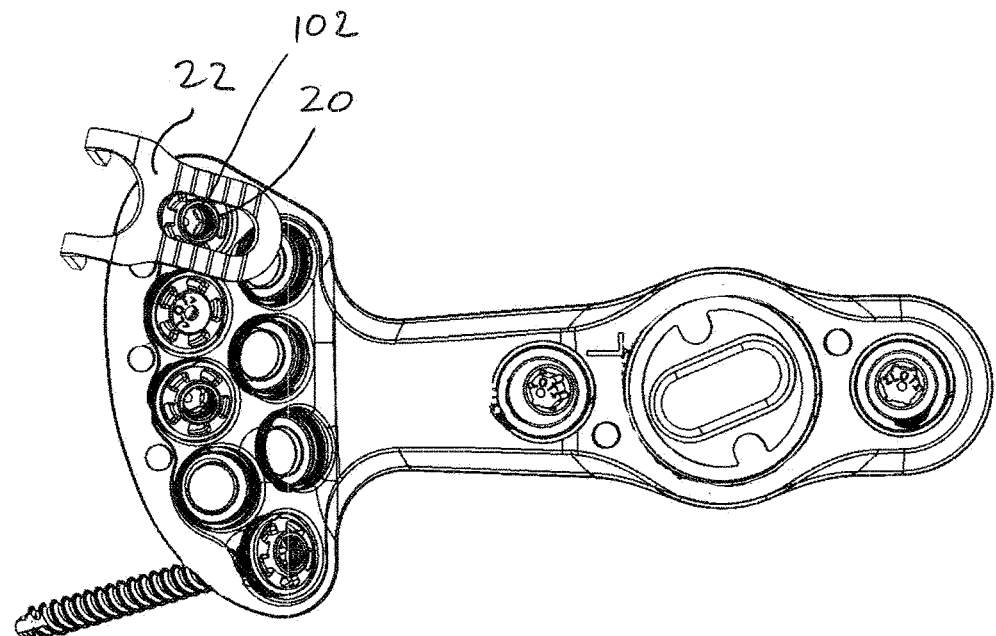
FIG. 18 is a top view of a bone plate assembly in which a hook accessory element is positioned over a second-type locking element.
Figure 20:
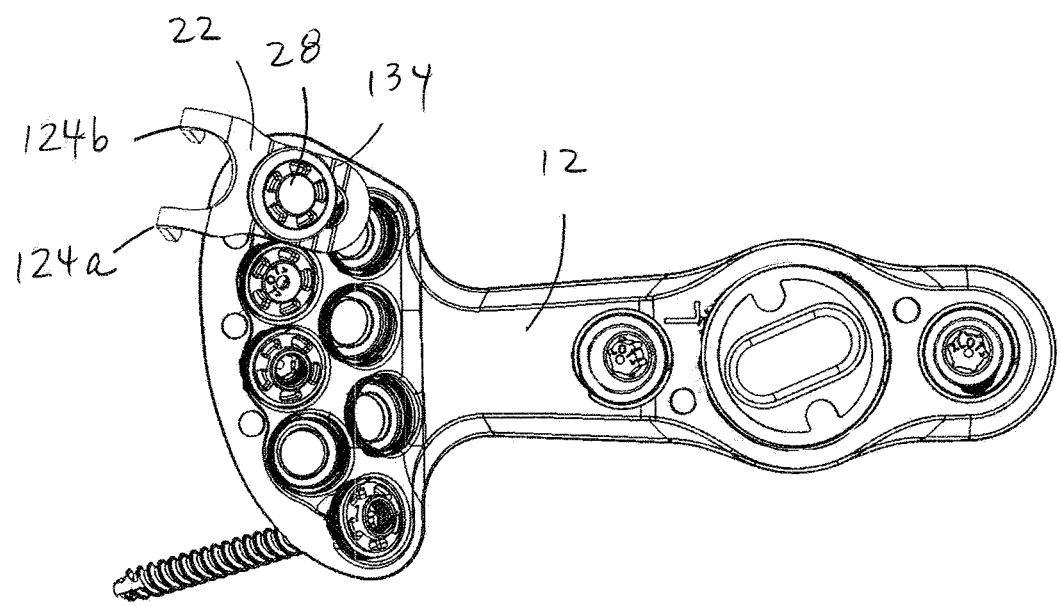
FIG. 20 is a top view of a bone plate assembly in which the hook accessory is secured relative to the plate with a retainer element engaged with the second-type element.
Figure 19A:
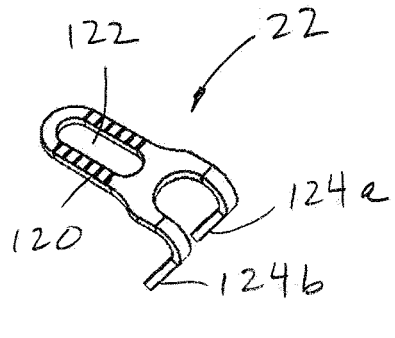
FIGS. 19a-19e are top perspective, bottom perspective, top, front and side elevation views, respectively, of the hook accessory shown as part of the bone plate assembly in FIG. 18.
Figure 19B:
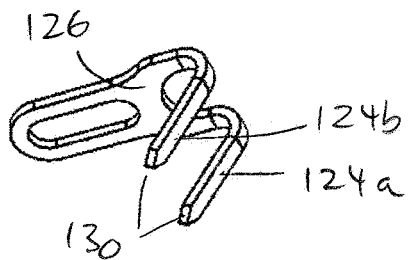
Figure 19C:
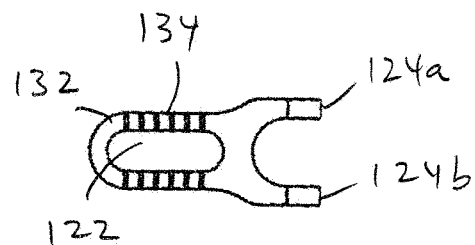
Figure 19D:
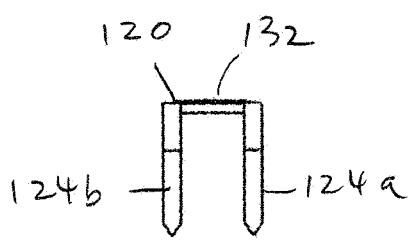
Figure 19E:
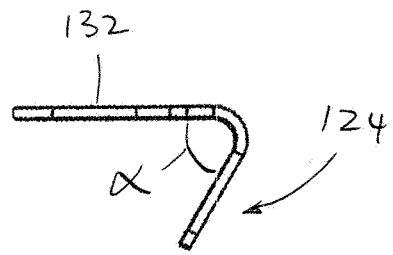

Then, referring to FIG. 18, in one example, an accessory element in the form of a hook element 22 is positioned over the second-type locking element 20. Turning to FIGS. 19a-19e, the hook element 22 includes a flat, plate-like, body portion 120 defining an elongate slot 122, and at least one hook member 124. The at least one hook member preferably includes two hook members 124a, 124b which can be spaced apart wider than the sides of the body portion 120. The hook members 124a, 124b extend at an angle α relative to a lower surface 126 of the body portion 120. The angle α is preferably between 45° and 90° relative to the body portion, and more preferably approximately 60°. The distal ends 130 of the hook members 124a, 124b are sharpened to pierce bone. The upper surface 132 of the body portion may include ribs 134 or other friction engaging textures. Referring to FIGS. 18 and 19, the slot 122 of the hook element 22 is positioned over the tubular extension 102 on the locking element 20 such that the hook element can be longitudinally displaced thereon. The hook may be engaged into the bone. The retaining element 28 is then threaded into the tubular extension of the locking element 20. The hook element can be longitudinally and angularly adjusted in position relative to the plate, and then the retaining element 28 is tightened against the body portion 120, frictionally enhanced by ribs 134 or other texture, to securely hold the hook element in position relative to the plate 12.

Figure 21:
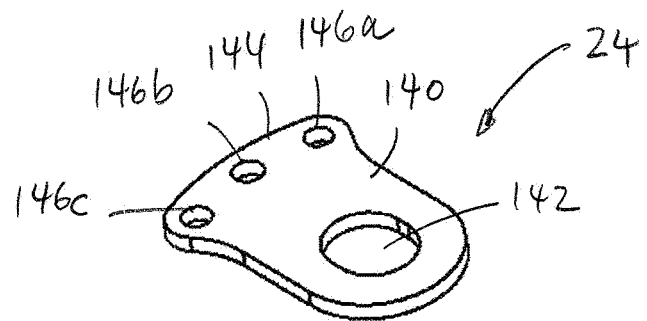
FIG. 21 is a perspective view of a suture retainer accessory for use in the bone plate assembly.
Figure 22:
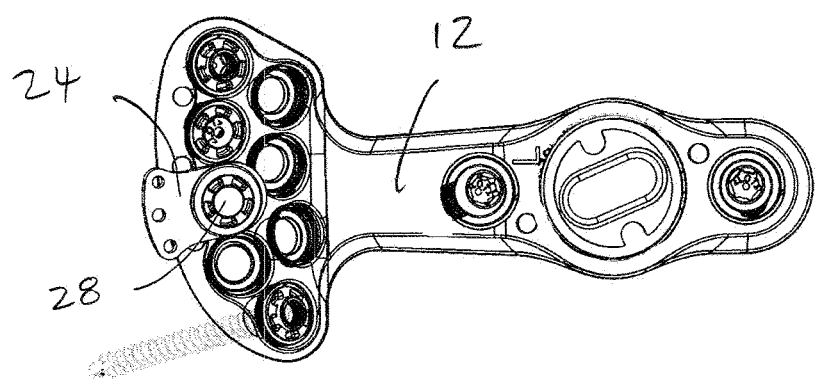
FIG. 22 is a top view of a bone plate assembly in which the suture retainer accessory is secured relative to the plate with a retainer element engaged with a second-type element.
Figure 23A:
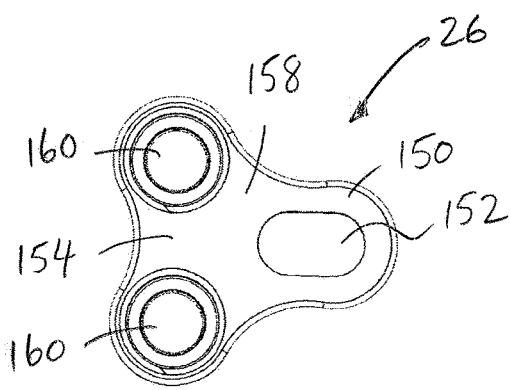
FIGS. 23a-23d are top, bottom, top perspective, and bottom perspective views, respectively, of a plate extender accessory.
Figure 23B:
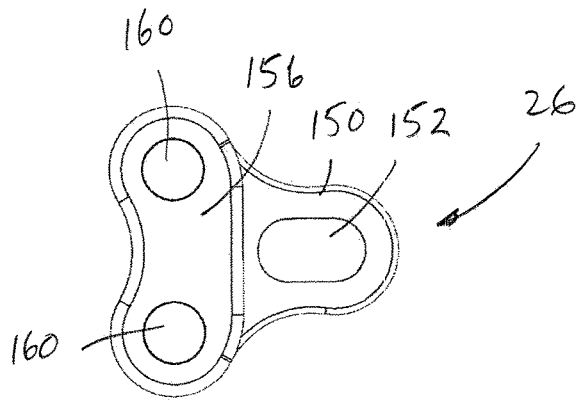
Figure 23C:
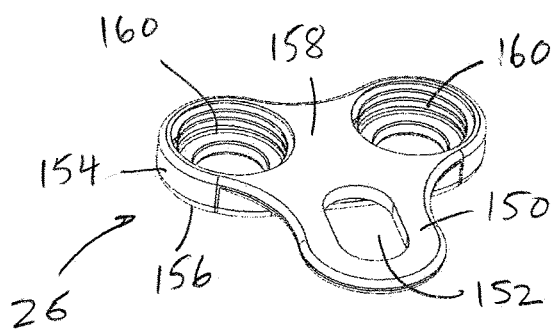
Figure 23D:
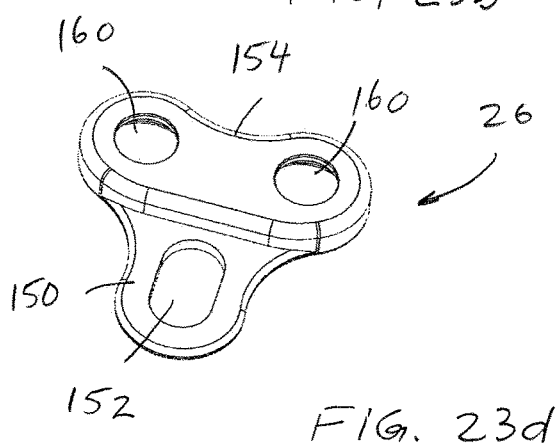

Turning now to FIG. 21, the suture retainer accessory element 24 is shown. The suture retainer accessory element 24 includes a flat, sheet-like body portion 140 with an elongate slot 142 and a distal portion 144 provided with a plurality of suture retention holes 146a, 146b, 146c. Referring to FIG. 22, the suture retainer 24 is shown attached to the plate 12 at a second-type locking element 20; i.e., by clamping the suture retainer between a retaining element 28 and a second-type locking element 20, wherein the second-type locking element can be already serving to locking the angular orientation and axial position of a bone fastener relative to the plate 12. Before fully tightening the retaining element, the suture retainer can be longitudinally and angularly adjusted relative to the plate 12. Once the suture retainer 24 is tightened, it can be used in conjunction with suture material to anchor soft tissue relative to the plate, or a bone anchor to secure a bone or bone fragment relative to the plate. In addition, while the holes 146a, 146b, 146c are shown formed straight through the body portion 120, one or more may be oriented at an oblique angle relative to surfaces of the body portion. In addition, one or more of the holes 146a, 146b, 146c may be sized to stably receive K-wires or other fixators in selected orientations.

Figure 24:
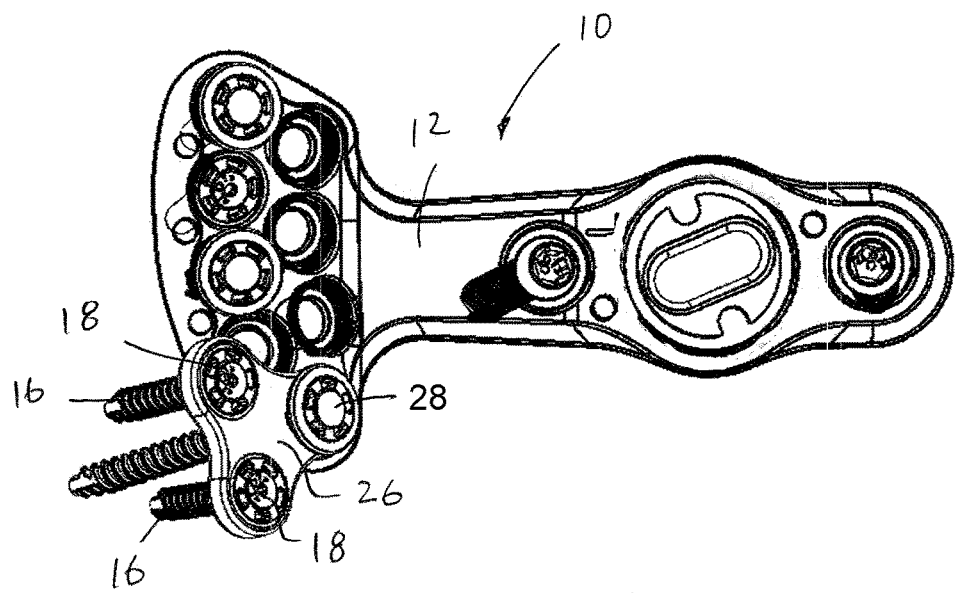
FIG. 24 is a top view of a bone plate assembly in which the plate extender accessory is secured relative to the plate with a retainer element engaged with a second-type element.
Figure 25A:
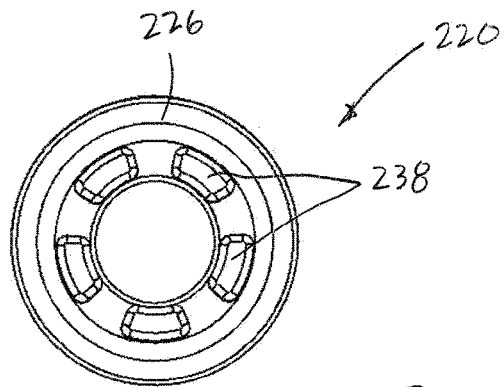
FIGS. 25a-25d are top, bottom, side, and perspective views, respectively, of another locking element of the system.
Figure 25B:
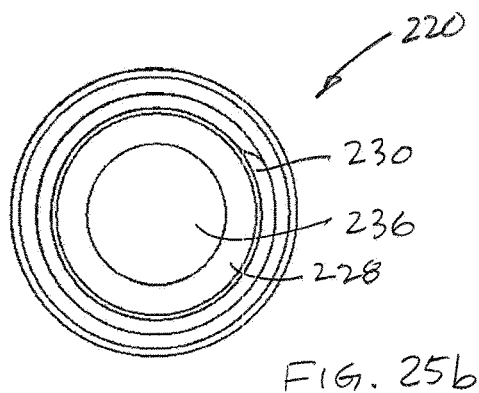
Figure 25C:
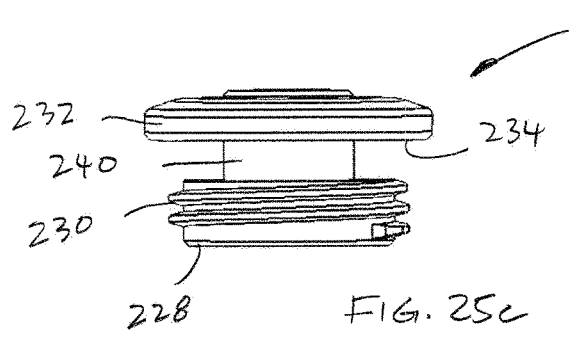
Figure 25D:
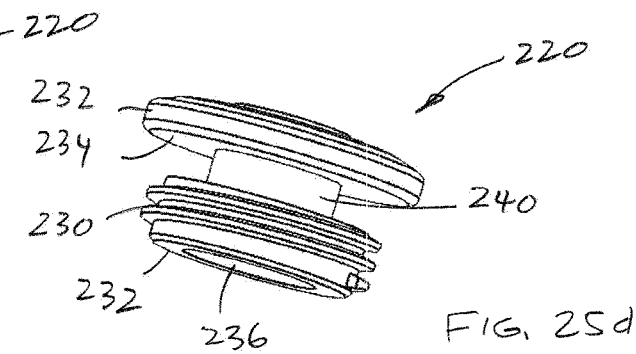

Turning now to FIGS. 23a-23d, a plate extender accessory 26 is shown for assembly relative to the plate. The plate extender accessory 26 includes a body portion 150 defining an elongate slot 152, and a head portion 154. The head portion defines at least one and preferably a plurality of screw holes 160 of similar structure to screw hole 40; i.e., such that screw holes 160 can accommodate a polyaxial fastener 14, 16, and a first-type locking element 18 or a second-type locking element 20. Thus, in accord with the teaching herein, the plate extender 26 permits attachment of additional accessory elements 22, 24, 26 thereto at its screw holes even when such screw holes have a bone fastener therein. The head portion 154 is preferably thicker in construct than the body portion 150 to accommodate the preferred structure of screw holes 140. The additional thickness of the head portion 154 is preferably presented at the lower surface 156 of the head portion such that the top surface 158 of the plate extender has a uniform smooth surface to minimize soft tissue irritation and the bottom surface at the head portion resides closer to the bottom surface of the plate 12. Referring to FIG. 24, the plate extender 26 is shown attached to the plate 12 at a second-type locking element 20; i.e., by clamping the plate extender between a retaining element 28 and a second-type locking element 20, wherein the second-type locking element can be already serving to locking the angular orientation and axial position of a bone fastener relative to the plate 12. Before fully tightening the retaining element, the plate extender can be longitudinally and angularly adjusted relative to the plate 12. Once the plate extender is secured, additional bone fasteners can be inserted through the screw holes 160 and into bone and locked in accord with the teachings herein. Alternatively, the screw holes in the plate extender 26 can use different mechanisms to receive bone fasteners in one or more of locked or non-locked engagements, and fixed angle and/or polyaxial orientations.

Figure 26:
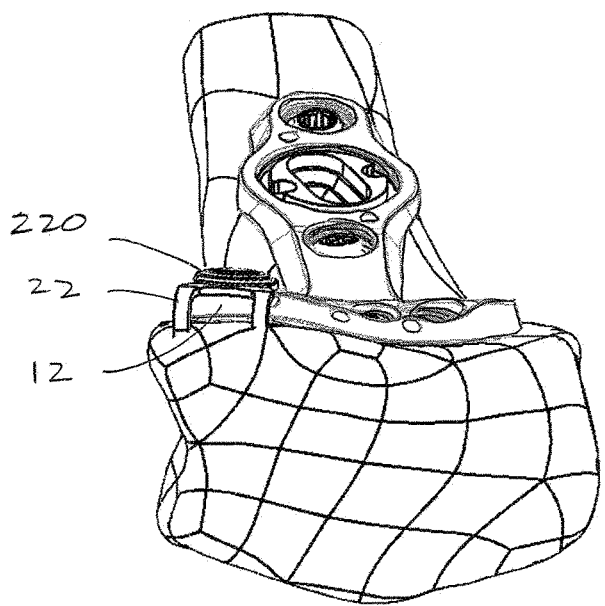
FIG. 26 is an illustration of a system using a plate, accessory element, and locking element of the type shown in FIGS. 25a-25d shown implanted on a distal radius bone.

Turning now to FIGS. 25a-25d, a third-type of locking element 220 is shown that eliminates the requirement for a separate and distinct retainer. The third-type locking element 220 is substantially cylindrical and has a top side 226 and a bottom side 228. Adjacent the bottom side 228, the element 220 includes a threaded exterior surface portion 230 which cooperates with the internally threaded portion 82 of the bore 80 of the screw hole in the plate 12 (FIG. 7). Adjacent the top side 226, the element 220 includes a cover portion 232 with a preferably flat lower surface 234. The cover portion 232 has a diameter at least as large as the threaded exterior surface, and preferably larger. A smaller diameter shaft 240 extends between the threaded exterior surface portion 230 and the cover portion 232. On the bottom side 228, the locking element 220 comprises preferably a spherically-shaped head recess 236 which fits to the spherically-shaped portion of the head 68. The depth of the head recess 236 can be equal to or larger than the radius of the spherical portion of the head 68. By means of this, the pressure exerted by the locking element 220 onto the head 68 is smoothly distributed onto the head 68. A driver recess 238 in form of a ring-shaped arrangement of one or more slots or grooves allows a form-fit engagement of a corresponding tool in the outer radial area of the top side 226 of the locking element 220. The height of the locking element 220 is greater than the depth of the bore 80 so that when the locking element 220 is screwed into the bore 80 its top side 86 sits above the plate member. More particularly, the slot openings in the accessory elements are sized to permit passage of the threaded portion 230 of the locking element 220 therethrough and so that the shaft 240 seats within the slot opening. Then, referring to FIG. 26, after longitudinal displacement or rotational adjustment of the accessory element 22 relative to the plate, the locking element 220 is threadedly tightened into the screw hole of the plate. As the locking element 220 is threadedly tightened, the head recess 236 in the lower side 228 of the locking element engages the head

68 of the bone fastener to fix the bone fastener relative to the plate, and the lower surface of the cover portion compresses against the accessory element 22 against the plate to fix the accessory element relative to the plate.

Turning back to FIGS. 1 and 2, it is appreciated that multiple accessory elements, hooks 22, suture retainers 24, and plate extenders 26, may be assembled relative to the plate. In addition, while not explicitly shown it is clearly evident that two or more of the same type of accessory element may be assembled to the plate. For example, multiple plate extenders can be attached to the plate. The system permits the described accessory elements as well as other accessory elements of various design and purpose to be assembled at bone fastener holes that already have bone fasteners previously installed and residing in the bone.

There have been described and illustrated herein embodiments of a plate assembly including accessory elements coupled to a bone plate and methods and systems therefor. While particular embodiments of the invention have been described, it is not intended that the invention be limited thereto, as it is intended that the invention be as broad in scope as the art will allow and that the specification be read likewise. The shape of the plate member is not restricted to the embodiments shown. Other shapes are also conceivable. Also, while a treatment of distal radius fractures is described, the plate assembly is not limited to such treatment. The bone anchor is not limited to a bone screw which has a threaded shank. Smooth, barbed or roughened pins are also conceivable. Further, any known bone fasteners may be used. Additionally, other bone anchors may be used. It will therefore be appreciated by those skilled in the art that yet other modifications could be made to the provided invention without deviating from its scope as claimed.

What is claimed is:

1. A bone plate assembly for stabilizing a bone fracture, comprising:
   a) a bone plate having a lower surface, an upper surface, and defining a screw hole extending between the upper and lower surfaces and having a lower portion and an upper portion and a central axis defined by the upper portion, the upper surface of the bone plate defining a perimeter of the bone plate;
   b) a first fastener extending through the screw hole and having a portion supported by the screw hole;
   c) an accessory element having an opening positioned at least partly over the first fastener, the accessory element extending over the perimeter of the bone plate; and
   d) a second fastener positioned over the first fastener and over the opening of the accessory element and coupled axially relative to the upper portion of the screw hole.

2. The bone plate assembly of claim 1, wherein the accessory element is one of a hook element, a suture retainer element, and a plate extender element.

3. A bone plate assembly for stabilizing a bone fracture, comprising:
   a) a bone plate defining a screw hole with a lower portion and an upper portion;
   b) a bone fastener having a head and a shaft, the bone fastener extending through the screw hole such that the head is supported in the lower portion of the screw hole;
   c) a locking element provided in the upper portion of the screw hole to prevent axial displacement of the bone fastener relative to the plate;
   d) an accessory element having an opening positioned at least partly over the locking element; and
   e) a retaining element positioned through the opening and coupled to the locking element to attach the accessory element to the bone plate.

4. A bone plate assembly for stabilizing a bone fracture, comprising:
   a) a bone plate defining an upper surface and a lower surface, a first screw hole and a second screw hole, each of the first and second screw holes extending between the upper surface and lower surface and having a lower portion and an upper portion;
   b) a first bone fastener having a head and a shaft, the first bone fastener extending through the first screw hole such that the head of the first bone fastener is supported in the lower portion of the first screw hole;
   c) a second bone fastener having a head and a shaft, the second bone fastener extending through the second screw hole such that the head of the second bone fastener is supported in the lower portion of the first screw hole;
   d) a first locking element provided in the upper portion of the first screw hole to prevent axial displacement of the first bone fastener relative to the plate;
   e) a second locking element provided in the upper portion of the second screw hole to prevent axial displacement of the second bone fastener relative to the plate;
   f) a first accessory element having an opening positioned at least partly over the first locking element;
   g) a second accessory element having an opening positioned at least partly over the second locking element;
   h) a first retaining element positioned through the opening and coupled to the first locking element to attach the first accessory element to the bone plate; and
   i) a second retaining element positioned through the opening and coupled to the second locking element to attach the second accessory element to the bone plate.

5. The bone plate according to claim 4, wherein the first and second accessory elements are different types of accessory elements.

6. The bone plate according to claim 5, wherein the first accessory element is one of a hook element, a suture retainer element, and a plate extender element, and the second accessory element is another of a hook element, a suture retainer element, and a plate extender element.

7. A system for stabilizing a bone fracture, comprising:
   a) a bone plate having a screw hole having a lower portion and an upper portion;
   b) a polyaxial bone fastener having a head with a spherical portion and a shaft, the head sized to be rotatably supported in the lower portion of the screw hole;
   c) a locking element having an outer portion that is rotationally engageable in the upper portion of the screw hole over the head of bone fastener to lock the axial position of the bone fastener relative to the plate, the locking element having an axial threaded opening;
   d) an accessory element provided with an opening positionable over the threaded opening the locking element; and
   e) a set screw receivable through the opening in the accessory element and threadable into the threaded bore of the locking element to secure a portion of the accessory element between the locking element and a portion of the set screw to retain the accessory element relative to the plate.

8. The system of claim 7, wherein the accessory element is one of a hook element, a suture retainer element, and a plate extender element.

9. A system for stabilizing a bone fracture, comprising:
a) a bone plate having a screw hole having a lower portion and an upper portion;
b) a bone fastener having a head and a shaft, the head sized to be received and supported in the lower portion of the screw hole;
c) a locking element having an outer portion that is rotationally engageable in the upper portion of the screw hole over the head of bone fastener to lock the axial position of the bone fastener relative to the plate, the locking element having an axial threaded bore;
d) an accessory element provided with an opening receivable over the threaded bore of the locking element; and
e) a retainer having a threaded shaft portion and a cover portion, the threaded shaft portion positionable through the opening in the accessory element and threadable into the threaded bore of the locking element to secure a portion of the accessory element between the locking element and the cover portion of the retainer to retain the accessory element relative to the plate.

10. A bone plate system for stabilizing a bone fracture, comprising:
a) a bone plate defining a screw hole with a lower portion defining a screw seat and an upper threaded portion;
b) a bone fastener having a head and a shaft, the head having a spherical surface adapted to be polyaxially supported in the screw seat;
c) an accessory element having an opening; and
d) a retainer having a threaded first portion adapted to be threadedly engaged with the upper threaded portion of the screw seat and apply force to the head of the bone fastener to secure the bone fastener relative to the bone plate, a second portion extendable within the opening of the accessory element, and a third portion adapted to apply a compressive force against the accessory element to secure the accessory element relative to the bone plate.

11. The system of claim 10, wherein the first portion has a first diameter, the second portion has a second diameter, and the third portion has a third diameter, and the second diameter is smaller than the first and third diameter.

12. The system of claim 10, wherein the second portion is non-threaded.

13. The system of claim 10, wherein the first portion has a lower surface defining a recess.

14. The system of claim 10, wherein the accessory element is a hook element, a suture retainer element, or a plate extender element.

15. The system of claim 10, wherein the retainer is a unitary retaining element.

* * * * *